United States Patent

Saurat et al.

Patent Number: 6,083,227
Date of Patent: Jul. 4, 2000

[54] BONE SCREW AND METHOD FOR MANUFACTURING SAID SCREW

[75] Inventors: Jean Saurat, Avrille; Stephane Bette, Paris, both of France

[73] Assignee: SOfamor S.N.C., Cedex, France

[21] Appl. No.: 09/158,422

[22] Filed: Sep. 21, 1998

[30] Foreign Application Priority Data

Sep. 22, 1997 [FR] France ................................. 97 11770

[51] Int. Cl.⁷ .................................................. A61B 17/56
[52] U.S. Cl. ................................ 606/73; 606/61; 411/426
[58] Field of Search .......................... 606/61, 73; 411/412, 411/423, 426

[56] References Cited

U.S. PATENT DOCUMENTS

| | | | |
|---|---|---|---|
| 5,456,685 | 10/1995 | Huebner | 606/73 |
| 5,505,731 | 4/1996 | Tornier | 606/61 |
| 5,738,685 | 4/1998 | Halm et al. | 606/61 |
| 5,814,046 | 9/1998 | Hopf | 606/61 |

FOREIGN PATENT DOCUMENTS

| | | |
|---|---|---|
| 497537 | 12/1950 | France . |
| 2642958 | 8/1990 | France . |
| 2697991 | 5/1994 | France . |
| 44 00 001 A1 | 7/1995 | Germany . |
| 44 47 686 A1 | 5/1997 | Germany . |
| WO 92/09817 | 6/1992 | WIPO . |

*Primary Examiner*—Michael Buiz
*Assistant Examiner*—Julian W. Woo
*Attorney, Agent, or Firm*—Woodard, Emhardt, Naughton, Moriarty & McNett

[57] ABSTRACT

Bone screw for osteosynthesis devices comprising a screwing head and a screw-threaded shank having a transition portion having a variable profile between two shank parts of different profiles. The threading has a constant pitch and a constant outside diameter, and includes cutting crests throughout its length, including in the transition region. According to one method for manufacturing this screw, there are machined on the transition portion of the shank threads of decreasing depth up to the end of this transition region, the threads along the transition portion defining truncated, non-cutting crests. There is removed from the threads on the transition portion a sufficient amount of material for converting the non-cutting crests into sharp, cutting crests. This method provides a screw with bone anchorage capability throughout the length of the thread.

30 Claims, 4 Drawing Sheets

BONE SCREW AND METHOD FOR MANUFACTURING SAID SCREW

BACKGROUND OF THE INVENTION

The present invention relates to bone screws for osteosynthesis devices, for example spinal osteosynthesis devices, and more particularly to an improved bone screw and method for making the same.

Screws are known in the art which have a cylindroconical shank extending from a head. The shank has a profile that includes a cylindrical portion and a conical portion. The thread on the shank of the screw defines a crest that becomes progressively flat in the conical portion of the shank. Consequently, the part of the thread with a truncated crest that is flat does not perform its bone anchorage function effectively, which may have an adverse effect on the fixation of the screw in porous bone or bone of poor quality. Thus, it is desirable to keep a cutting crest throughout the length of the thread in order to ensure proper bone anchorage.

The present invention is directed towards meeting this and other needs and to provide further benefits and advantages.

SUMMARY OF THE INVENTION

According to one aspect of the present invention, a bone screw is provided including a head portion with a length of a shank extending from the head. The shank has a generally cylindrical end portion opposite the head portion, a variable transition portion between the end portion and the head portion, and a thread extending along the length of the shank. The thread has a generally constant pitch and a generally constant diameter along the length of the shank. The thread also has a depth that is generally constant along the end portion and progressively decreases along the transition portion in a direction from the end portion toward the head portion. The thread has an end closest to the head portion that defines a cutting crest. Preferably, the threading comprises a cutting crest throughout its length including in the transition region up to the end of the latter at which the last thread tapers away.

A screw provided with such a threading more effectively performs its bone anchorage function than screws produced heretofore. In one embodiment, the shank includes a generally smooth, unthreaded portion between the head and the transition portion. In another embodiment, the generally variable profile defines a frusto-conical shape. In yet another embodiment, the cutting crest defines a pointed edge.

According to another aspect of the present invention, a method for making the bone screw is provided. The method includes the steps of: (a) providing a blank having a shank extending from a head, the shank having a length with a generally constant diameter; (b) forming a thread along the length of the shank, the thread defining a cutting crest portion and a truncated crest portion, the thread having a generally constant pitch along the length; and (c) converting the truncated crest portion to another cutting crest portion by removing flank material from the truncated crest portion.

In one embodiment of the method, the thread made according to step (b) includes a first portion with a generally constant depth and a second portion with a progressively decreasing depth in a direction toward said head. In another embodiment, the converting step includes removing flank material from a front side and a rear side of the thread of the truncated crest portion. In still another embodiment, there is removed from the last threads a sufficient amount of material to convert the non-cutting truncated crests into sharp and cutting crests. In one embodiment of this manufacturing method, the material comprising the flank portions may be removed on either of the two sides of each thread, or in succession on both sides.

This method may be carried out by various means, for example milling, a numerical turning operation, rolling, or grinding apparatus. Two or three further successive passes of the tool may be necessary.

Accordingly, one object of the present invention is to provide a bone screw with improved anchorage capability.

It is another object to provide a bone screw with two or more portions having different profiles with a common thread having a generally uniform cutting crest, and generally constant diameter and pitch.

It is an additional object to manufacture a bone screw having a thread with a generally uniform cutting crest along a variable profile portion.

Further objects, aspects, features, benefits and advantages of the present invention shall become apparent from the description and drawings provided herewith.

DESCRIPTION OF THE PREFERRED EMBODIMENTS

Figure 1:
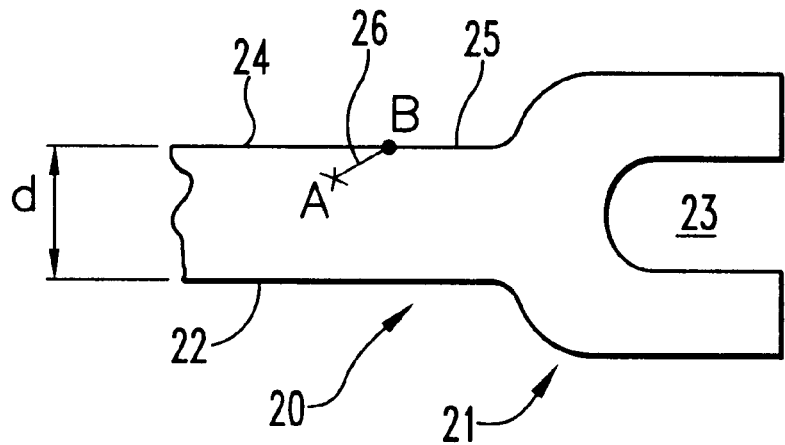
FIG. 1 is a simplified partial longitudinal elevational view of the bone screw in which a transition region is indicated between two parts of the shank of different profiles.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

Shown in FIG. 1 is a bone screw 20 intended for osteosynthesis devices, for example vertebral osteosynthesis devices, comprising a screw head 21 for screwing by means of a tool (not shown) and a screw-threaded shank 22 extending from the screw head 21. The head 21 has a U-shaped profile defining a central slot 23 adapted to receive a member (not shown), for example a shank of a spinal osteosynthesis device. It is also contemplated that other profiles of head 21 be provided as would occur to those skilled in the art. The shank 22 comprises two parts or portions 24 and 25 whose profiles are different and of any type, and an intermediate transition region or portion 26 between the parts 24 and 25 extending from the end A of the part 24 to the end B of the part 25. This region 26 has a variable transition profile which may be, for example, frusto-conical in shape as illustrated, and is connected at B to the surface of the shank part 25. In one embodiment, part 25 is smooth while the part 24 is screw threaded, and the diameter "d" of the thread on part 24 is equal to the diameter of the smooth part 25. Among the objects of the invention is to produce in the transition region 26 a thread with crests (not shown) that remain cutting crests from the end A of part 24 up to the end B of the junction with the part 25.

Figure 2:
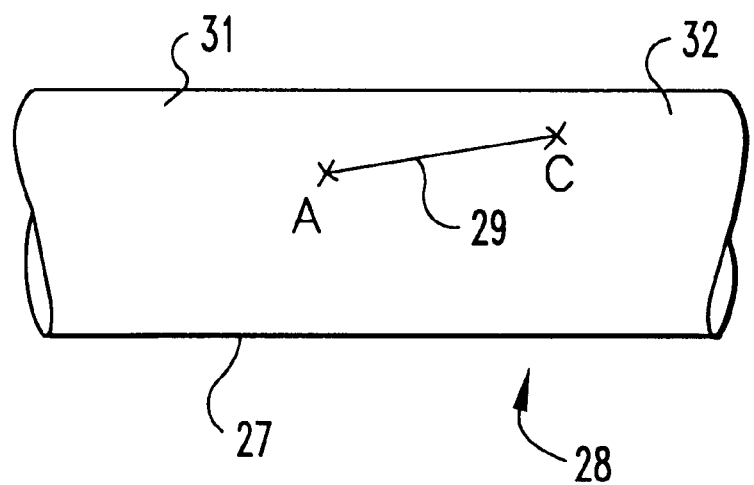
FIG. 2 is a simplified partial elevational view of the shank of a bone screw indicating a transition region of its shank which is different from the transition region of FIG. 1.

Referring now to the screw-threaded shank 27 of the screw 28 shown in FIG. 2, the transition region 29 connects a point A of the shank part or portion 31 to a point C of a second shank part or portion 32 with parts 31 and 32 being screw threaded. The transition region 29 has a variable transition profile that is frusto-conical in shape, but the point C is situated at the base of the threads of the shank part 32 and not at the level of a smooth surface, such as that of the part 25 of FIG. 1. In this case also, another of the objects of the invention is to produce in the transition region 29 threads whose cutting crests remain cutting from the point A of part 31 up to the point C of part 32.

Figure 3:
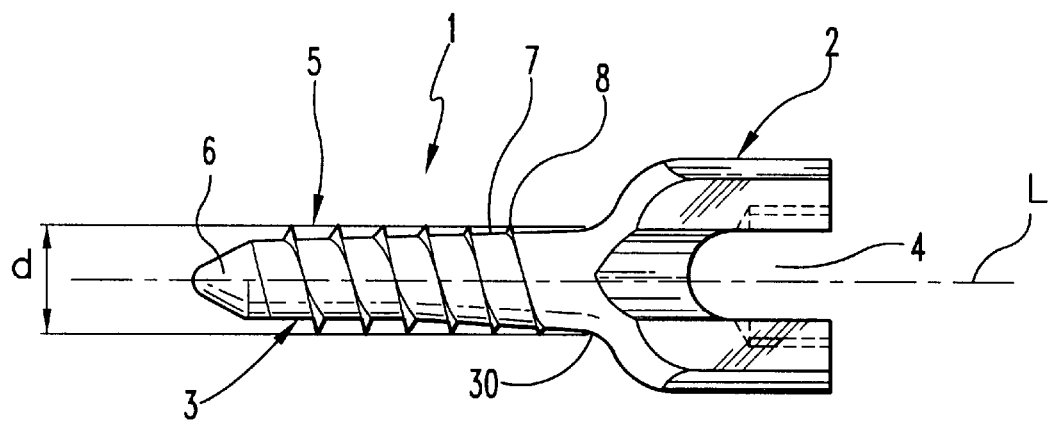
FIG. 3 is an elevational view to a larger scale of one embodiment of the bone screw according to the invention.
Figure 4:
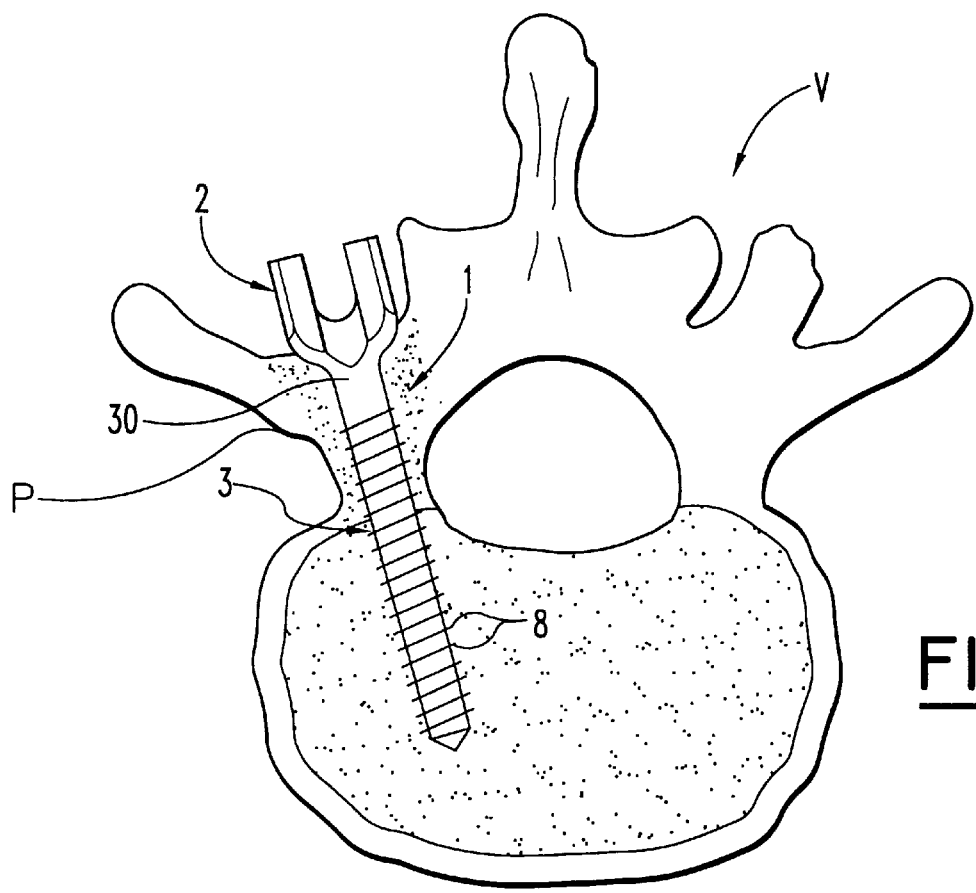
FIG. 4 is a diagrammatic elevational view of the implantation of a bone screw in a vertebral pedicle.

In one embodiment, bone screw 1 of FIGS. 3 and 4 comprises a head 2 and a screw-threaded shank 3. Bone screw 1 is shown along its longitudinal axis L. The head 2 has a U-shaped profile and defines a central slot 4 which may receive a member (not shown) such as the shank of a spinal osteosynthesis device. The shank 3 comprises a cylindrical end part or portion 5 extended by a point 6, and a transition portion or conical profile part 7 between cylindrical part 5 and head 2. Part 7 constitutes a portion forming a transition region having a frusto-conical shape or profile between part 5 and a smooth portion or part 30 connected to head 2. The shank 3 is provided with a threading 8 having a diameter "d" that is generally constant from point 6 to the smooth part 30. Threading 8 also has a generally constant pitch "p" as measured from the rear flanks of the threads.

Part 7 constitutes a portion forming a transition region between the part 5 and smooth part 30 connected to the head 2. As shown more clearly in FIGS. 5 and 6, in the depicted embodiment, the part 5 has a cylindrical profile contour 5a that corresponds to a right cylindrical shape. Part 7 has a frusto-conical profile contour 7a that corresponds to a frusto-conical shape. Both the right cylindrical shape and frusto-conical shape may correspond to surfaces of revolution about axis L.

Figure 5:
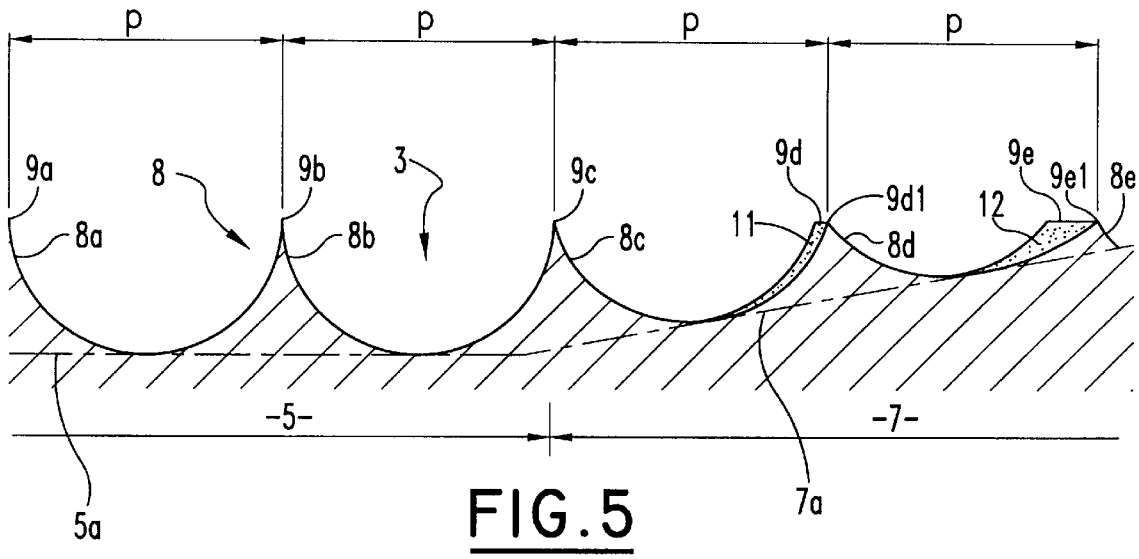
FIG. 5 is a partial sectional view to a larger scale of the shank of the bone screw of FIG. 3, showing its threads before the machining of the last crests of its transition region of the threaded shank.
Figure 6:
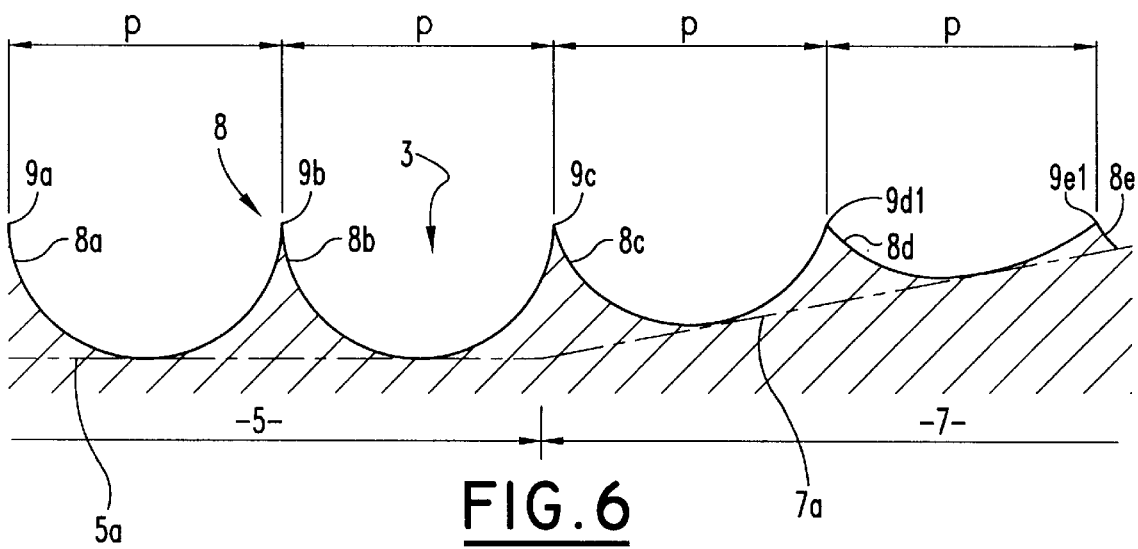
FIG. 6 is a view of the shank of FIG. 5 after machining in accordance with the invention of the last threads of the transition region.

The threading 8 comprises a number of thread portions 8a–8e which are illustrated in FIGS. 5 and 6. Portions 8a–8e have respective cutting crests 9a–9e throughout their length, including the last crests 9d and 9e at the end adjacent to the head 2. Along the part 7, the portion of thread 8 designated as 8d and 8e taper away. It should be understood that the taper of threading 8 may vary as would occur to one skilled in the art.

The form of the thread 8 shown in FIG. 6 differs from the forms of the threads of the known prior screws and more precisely in the non-cylindrical part of their shank, by the fact that, in these prior screws, the last thread portions 8d, 8e do not have cutting crests 9d1, 9e1, but truncated crests 9d, 9e. The truncated crests 9d, 9e have planar faces parallel to the axis of the screw in the sectional view of FIG. 5. The truncated crests are constituted in part to an amount of non-milled material or flank portions 11 and 12, constituting one of the flanks of a corresponding one of the thread portions 8d, 8e. The thread form 8 illustrated in FIG. 6 conforms to the invention since the thread portions 8d and 8e terminate in cutting crests 9d1 and 9e1.

To obtain the cutting crests 9d1 and 9e1, various procedures may be adopted for removal of flank portions 11 and 12, such as numerical turning, milling, grinding, or by rolling, molding or grinding. First, there is machined in the conventional manner, for example, by means of a milling cutter (not shown) the cylindrical part 5 and the transition part 7 of the shank 3 to obtain thread portions 8a–8e of thread 8. The thread portions 8a–8e have a generally constant depth along first portion 5 and have a depth progressively decreasing in the direction toward the end or head 2 of the screw 1 along transition portion 7 of shank 3. The thread 8 has a constant pitch "p" and a constant diameter "d." At the end of this first stage, a thread 8, such as that of FIG. 5, is obtained whose last thread portions 8d, 8e have truncated non-cutting crests 9d, 9e. This is due to the fact that the progressive radial rearward withdrawal of the milling cutter removes less material from the blank and consequently leaves thread portions 8d, 8e with thickened flanks 11, 12, respectively, resulting in truncated crests 9d, 9e. The milling cutter is then made to effect at least one additional pass, and preferably two or three passes, on these last-mentioned thread portions 8d, 8e so as to remove amounts of flank material 11, 12 sufficient to convert the non-cutting truncated crests 9d, 9e into sharp and cutting crests 9d1 and 9e1, resulting in the thread form of FIG. 6.

The threading 8 produced in this way therefore comprises cutting crests 9a, 9b, 9c, 9d1, and 9e1 throughout its length, including up to the end of the transition part 7. In a preferred embodiment, the end of the last thread portion 8e tapers away on the shank 3. The material comprising flank portions 11, 12 may be removed on either of the sides of the thread portions 8d and 8e. In one embodiment, the material comprising flank portions 11 and 12 is removed from both sides of each of the thread portions 8d and 8e. The bone screw 1 having a threading 8 with a cutting crest throughout its length more effectively performs its bone anchorage function than the prior screws. FIG. 4 shows the positioning of a screw 1 according to the invention in a pedicle P of a vertebra V. The threaded shank 3 is screwed into a relatively narrow bone part of the vertebral body. Thus, benefits of the present invention are particularly well illustrated. Providing cutting crests on the whole of the threading 8 improves the gripping capabilities of the screw 1 along the entire length of the shank, and also allows for easier insertion into the vertebra V.

Figure 7:
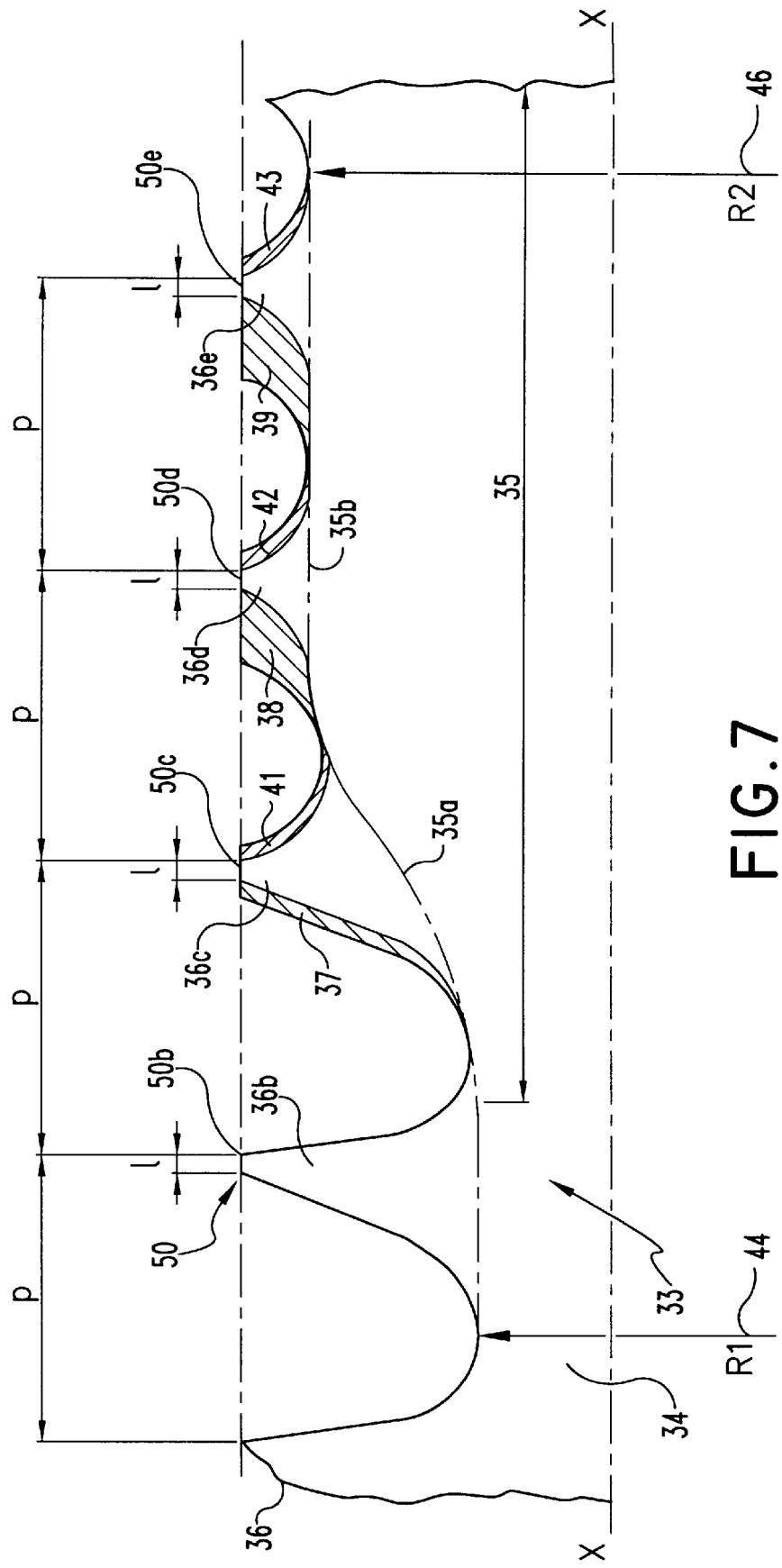
FIG. 7 is a partial sectional view to a larger scale of a shank of a bone screw according to another embodiment of the invention.

In the embodiment of FIG. 7, the screw having a longitudinal axis xx comprises a screw-threaded shank 33 with a first threaded part or portion 34. A transition region or portion 35 is also threaded and connected to a third part or portion (not shown), which may have any profile.

The threading 36 has a constant pitch "p" (measured from the rear of thread of the screw) and extends from the part 34 through the transition region 35. Transition region 35 includes a substantially frusto-conical part or portion 35a, which is connected to the profile of the part 34, and a cylindrical part or portion 35b connected to the part 35a, which extends to a third portion or a head (not shown). In the parts 35a and 35b, the thread 36 has a depth which decreases with respect to its depth in the shank part 34. The threads 38 thus define a shank 33 having a first root diameter (R1) 44 that increases to a second root diameter (R2) 46. The root diameter of the shank varies along the transition portion 35 from the first root diameter 44 to the second root diameter 46.

Before carrying out the method according to the invention, the crests 50 of the threads 36 in the region 35 have non-cutting truncated parts 50c, 50d, 50e which include flank material in the hatched regions 37, 41, 38, 42, 39, and 43. The flank material may be removed solely on the front of the thread (hatched regions 37, 38, 39), or on the front of the threads and on the rear of the threads (hatched regions 41, 42, 43), while leaving a truncated part at the top of the threads having a width "1."

Thus, there remains a small truncated part of width "1" at the top of the crests of the thread 36 throughout the length of the shank 33, the width "1" of this truncated part being generally constant. However, it should be understood that this length "1" is small such that the crests 50 still effectively function as cutting crests. This is true even if solely the regions 37, 38, 39, or if solely the regions 41, 42, 43, are removed in order to reduce the cost of this additional machining. Consequently, the truncation of the crests 50 of the end threads in the transition region 35 is sufficiently small to enable the corresponding threads to be cutting threads and solve the problem in accordance with the invention.

French Patent Application No. 97 11 770 to jean saurat et al, filed Sep. 22, 1997, and to which priority is claimed, is hereby incorporated by reference as if it were set forth in its entirety herein.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone screw, comprising:
  a head portion;
  a shank defining a length, said shank extending from said head portion and including:
    an end portion opposite said head portion having a generally cylindrical profile;
    a transition portion between said end portion and said head portion having a variable profile; and
    a thread extending along said length having a generally constant pitch and a generally constant diameter along said length, said thread having a depth that is generally constant along said end portion and progressively decreases along said transition portion in a direction from said end portion toward said head portion, and has an end closest to said head portion with a cutting crest.

2. The bone screw of claim 1, wherein said shank includes a generally smooth, unthreaded portion between said head portion and said transition portion.

3. The bone screw of claim 1, wherein said generally variable profile defines a frusto-conical shape.

4. The bone screw of claim 1, wherein said cutting crest defines an edge for engaging bone, and said edge terminates in an apical point on a cross section of said shank taken parallel to the length of said shank.

5. The bone screw of claim 1, wherein said cutting crest extends along the entire length of said thread.

6. The bone screw of claim 1, wherein said head has a generally U-shaped profile defining a slot.

7. A method for manufacturing a bone screw, comprising the steps of:
  (a) providing a blank having a shank extending from a head, the shank having a length with a generally constant diameter;
  (b) forming a thread along the length of the shank, the thread defining a cutting crest portion and a truncated crest portion, the thread having a generally constant pitch along the length; and
  (c) converting the truncated crest portion to another cutting crest portion by removing flank material from the truncated crest portion.

8. The method according to claim 7, wherein the thread made according to step (b) includes a first portion with a generally constant depth and a second portion with a progressively decreasing depth in a direction toward said head.

9. The method according to claim 7, wherein the forming step and the converting step are performed by a milling cutter.

10. The method according to claim 9, further comprising gradually withdrawing the milling cutter to define a transitional portion, the thread having a progressively decreasing depth along the transitional portion in a direction toward the head along the shank.

11. The method according to claim 7, wherein the converting step includes removing the flank material from a front side of the thread of the truncated crest portion.

12. The method according to claim 7, wherein the converting step includes removing a flank material from a front side and a rear side of the thread of the truncated crest portion.

13. The method of claim 7, wherein the forming step includes milling, rolling, grinding, or molding.

14. The method of claim 7, wherein the bone screw provided by the converting step includes:
  an end portion opposite the head, the end portion having a generally cylindrical profile, the thread having a generally constant depth along said end portion;
  a transition portion between the end portion and the head portion, the transition portion having a generally frusto-conical profile, the thread having a progressively decreasing depth in a direction from the end portion toward the head; and
  further wherein the thread has a generally constant diameter.

15. The method of claim 7, wherein the head has a generally U-shaped profile defining a slot.

16. A bone screw, comprising:
  a head portion having a generally U-shaped profile defining a slot;
  a shank defining a length, said shank extending from said head portion and including:
    an end portion opposite said head portion having a generally cylindrical profile;
    a transition portion between said end portion and said head portion having a variable profile; and
    a thread having a depth that is generally constant along said end portion and progressively decreases along said transition portion in a direction from said end portion toward said head portion, and has an end closest to said head with a cutting crest.

17. The bone screw of claim 16, wherein said shank includes a generally smooth, unthreaded portion between said head portion and said transition portion.

18. The bone screw of claim 16, wherein said generally variable profile defines a frusto-conical shape.

19. The bone screw of claim 16, wherein said thread extends along said length with a generally constant pitch and a generally constant diameter, and said cutting crest extends along the entire length of said thread.

20. The bone screw of claim 16, wherein said cutting crest terminates an apical edge.

21. A bone screw, comprising:

a head portion;

a shank defining a length, said shank extending from said head portion and including:
- an end portion opposite said head portion having a generally cylindrical profile;
- a transition portion between said end portion and said head portion having a variable profile;
- a thread having a depth that is generally constant along said end portion and progressively decreases along said transition portion in a direction from said end portion toward said head portion, and has an end closest to said head with a cutting crest; and wherein said shank includes a generally smooth, unthreaded portion between said head portion and said transition portion.

22. The bone screw of claim 21, wherein said generally variable profile defines a frusto-conical shape.

23. The bone screw of claim 21, wherein said cutting crest defines an apical edge for engaging bone.

24. The bone screw of claim 21, wherein said thread extends along said length with a generally constant pitch and a generally constant diameter.

25. The bone screw of claim 21, wherein said head has a generally U-shaped profile defining a slot.

26. A bone screw, comprising:

a head portion;

a shank defining a length, said shank extending from said head portion and including:
- an end portion opposite said head portion having a generally cylindrical profile;
- a transition portion between said end portion and said head portion having a variable profile;
- a thread having a depth that is generally constant along said end portion and progressively decreases along said transition portion in a direction from said end portion toward said head portion, and has an end closest to said head with a cutting crest; and wherein said cutting crest defines an edge for engaging bone, and said edge terminates in an apical point on a cross section of said shank taken parallel to the length of said shank.

27. The bone screw of claim 26, wherein said shank includes a generally smooth, unthreaded portion between said head portion and said transition portion.

28. The bone screw of claim 26, wherein said generally variable profile defines a frusto-conical shape.

29. The bone screw of claim 26, wherein said thread extends along said length with a generally constant pitch and a generally constant diameter, and said cutting crest extends along the entire length of said thread.

30. The bone screw of claim 26, wherein said cutting crest terminates in an apical edge.

* * * * *